US011273912B2

(12) United States Patent
Chundi (10) Patent No.: US 11,273,912 B2
(45) Date of Patent: Mar. 15, 2022

(54) TRAFFIC STOP DRONE

(71) Applicant: Venkata Rama Subba Rao Chundi, Cumming, GA (US)

(72) Inventor: Venkata Rama Subba Rao Chundi, Cumming, GA (US)

(*) Notice: Subject to any disclaimer, the term of this patent is extended or adjusted under 35 U.S.C. 154(b) by 217 days.

(21) Appl. No.: 16/684,555

(22) Filed: Nov. 14, 2019

(65) Prior Publication Data

US 2020/0164981 A1 May 28, 2020

Related U.S. Application Data

(60) Provisional application No. 62/772,491, filed on Nov. 28, 2018.

(51) Int. Cl.
| | | |
|---|---|---|
| *B64C 39/02* | (2006.01) |
| *G06K 9/00* | (2006.01) |
| *G05D 1/00* | (2006.01) |
| *G05D 1/10* | (2006.01) |
| *B64D 1/00* | (2006.01) |
| *B64D 47/08* | (2006.01) |

(Continued)

(52) U.S. Cl.
CPC .............. *B64C 39/024* (2013.01); *B64D 1/00* (2013.01); *B64D 47/08* (2013.01); *G05D 1/0088* (2013.01); *G05D 1/106* (2019.05); *G06K 9/0063* (2013.01); *G06K 9/00288* (2013.01); *H04W 4/40* (2018.02); *B64C 2201/12* (2013.01); *B64C 2201/146* (2013.01); *B64C 2201/208* (2013.01); *G01N 33/4972* (2013.01); *G01S 15/86* (2020.01); *G01S 15/93* (2013.01); *G01S 19/13* (2013.01); *G06N 20/00* (2019.01)

(58) Field of Classification Search
CPC .............. B64C 39/024; B64C 2201/12; B64C 2201/127; B64C 2201/146; B64C 2201/208; B64D 1/00; B64D 47/08; G01N 33/4972; G01S 15/86; G01S 15/93; G01S 19/13; G05D 1/0088; G05D 1/106; G06K 9/00288; G06K 9/0063; G06N 20/00; G09F 21/08; H04W 4/40
USPC .......................................................... 701/11
See application file for complete search history.

(56) References Cited

U.S. PATENT DOCUMENTS 9,409,645 B1 * 8/2016 Sopper .................... H04L 67/10
9,471,059 B1 * 10/2016 Wilkins ............... G05D 1/0094
(Continued)

FOREIGN PATENT DOCUMENTS

WO WO-2014106814 A2 * 7/2014 ............. H04N 5/247

*Primary Examiner* — Joshua E Rodden (57) ABSTRACT

The present invention discloses a drone or unmanned aerial vehicle (UAV) mounted on a law enforcement vehicle for the purposes of interfacing with occupants of a stopped vehicle after being pulled over for a traffic violation or routine stop. The drone is equipped with a navigation system, obstacle-avoidance sensors, a telepresence system (a camera, microphone, speaker and screen), and a robotic arm with a secure box and a device for estimating blood alcohol content. Once a suspect vehicle has been pulled over by a law enforcement officer, without leaving the safety of a law enforcement vehicle, the officer deploys the drone to perform a visual check of the interior of the suspect vehicle for dangerous items, ascertain if an occupant's face triggers any flags on a central database, administer a sobriety test, collect the necessary documents and deliver a citation to the driver via the secure box.

9 Claims, 12 Drawing Sheets

(51) Int. Cl.
*H04W 4/40* (2018.01)
*G06N 20/00* (2019.01)
*G01S 15/86* (2020.01)
*G01S 15/93* (2020.01)
*G01S 19/13* (2010.01)
*G01N 33/497* (2006.01)

(56) References Cited

U.S. PATENT DOCUMENTS

| | | | |
|---|---|---|---|
| 9,836,117 B2* | 12/2017 | Shapira | G06F 3/011 |
| 10,067,502 B1* | 9/2018 | Delp | G06Q 10/20 |
| 10,145,684 B1* | 12/2018 | Tofte | G01C 11/02 |
| 10,198,954 B2* | 2/2019 | Holtzman | G05D 1/0088 |
| 10,427,786 B2* | 10/2019 | Shaw | G06F 21/32 |
| 10,492,012 B2* | 11/2019 | Cabouli | H04W 4/30 |
| 10,668,997 B2* | 6/2020 | Moses | B63C 9/01 |
| 10,696,397 B2* | 6/2020 | Sekine | G05D 1/0011 |
| 2015/0344136 A1* | 12/2015 | Dahlstrom | B64C 39/024 |
| | | | 701/3 |
| 2016/0332748 A1* | 11/2016 | Wang | B64F 1/22 |
| 2017/0129602 A1* | 5/2017 | Alduaiji | B60S 3/06 |
| 2017/0137125 A1* | 5/2017 | Kales | G09F 21/10 |
| 2017/0201714 A1* | 7/2017 | Kim | H04N 5/265 |
| 2017/0251181 A1* | 8/2017 | Smolyanskiy | G05D 1/005 |
| 2017/0253330 A1* | 9/2017 | Saigh | B64C 39/024 |
| 2017/0301234 A1* | 10/2017 | Park | H04R 27/00 |
| 2018/0174448 A1* | 6/2018 | Gomez Gutierrez | G08G 1/08 |
| 2019/0188814 A1* | 6/2019 | Kreitzer | G06Q 50/265 |
| 2020/0001994 A1* | 1/2020 | Prokhorov | G08G 5/0021 |
| 2020/0033846 A1* | 1/2020 | Buyse | G05D 1/0022 |
| 2020/0250994 A1* | 8/2020 | Corsica | G08G 5/0069 |
| 2021/0250806 A1* | 8/2021 | Santhar | H04W 28/0226 |

* cited by examiner

TRAFFIC STOP DRONE

This application claims the priority of U.S. Provisional Patent application No. 62/772,491, filed on Nov. 28, 2018. The present invention relates to safety of police and law enforcement officers, and more specifically for the safety of a law enforcement officer during a Traffic Stop. The invention adds an autonomous unmanned aerial vehicle, commonly known as a "drone", as a tool for an officer to avoid leaving their vehicle during a traffic stop. The drone is equipped with sensors and artificial intelligence to assist it in making the first, and, in some cases, only contact with an occupant of stopped suspect vehicle.

BACKGROUND

According to statistics collected by the FBI, 22 law enforcement officers were killed outside their vehicles during Traffic Pursuits/Stops between 2006 and 2015 (https://ucr.fbi.gov/leoka/2015/tables/table_25_leos_fk_during_traffic_pursuits_stops_activity_of_vo_by_location_of_offender_at_scene_of_incident_2006-2015.xls). According to the report by the Department of Justice, Office of Community Oriented Policing Services (COPS Office), Deadly Calls and Fatal Encounters, produced by the National Law Enforcement Officers Memorial Fund (NLEOMF) and funded by the COPS Office, over a five-year period (2010-2014) (http://www.nleomf.org/programs/cops/cops-report.html), "Traffic Stops accounted for 26 (63 percent) of the 41 self-initiated cases that lead to line of duty fatalities. Enforcing traffic regulations represent the most common form of contact the public has with law enforcement." Eleven of these fatalities were during contact with the vehicle occupants.

A routine traffic stop can turn deadly for an officer if the suspect vehicle's occupant intends to use a firearm, or a passing vehicle accidentally swerves and hits the officer as the officer is outside the law enforcement vehicle.

With the exception of the District of Columbia, every State has a "Move Over" law, which requires motorists to vacate the lane closest if safe and possible to do so, or slow to a safe speed. This law was enacted to save the lives of law enforcement officers.

Injuries and deaths of law enforcement officers can be avoided if the officer is not forced to leave the safety of his vehicle to conduct a traffic stop. However, a traffic stop requires the officer to leave their vehicle several times: to speak with the driver or get their license and registration, return to the law enforcement vehicle, return the documents, administer a sobriety test, and possibly deliver a traffic violation ticket. To date, there is no other way an officer can perform their duties without risking getting hit by a passing car, or shot by an occupant in the suspect vehicle.

There is known U.S. Pat. No. 9,471,059 for "UNMANNED AERIAL VEHICLE ASSISTANT", in which an embodiment shows a UAV docked on the officer's radio microphone or on the dash or center console of a law enforcement cruiser. This patent discloses that the officer can command the UAV to hover or follow him, and the UAV can then record audio and/or video of the officer's interaction with a citizen. The UAV can capture data about the vehicle such as license plate number and the driver's face. In this patent, the UAV serves as an autonomous airborne body camera or dash camera rather than an interface between the officer and the driver. The officer still has to leave the law enforcement vehicle to interact with the suspect vehicle occupants, and therefore puts himself at risk of getting shot or hit by a car.

OBJECT OF THE PRESENT INVENTION

The present invention will save law enforcement officers' lives. The traffic stop is one of the more dangerous actions a law enforcement officer has to undertake, and this invention will add an interface layer between the officer and the suspect vehicle's occupants. This interface is in the form of an autonomous UAV ("drone") mounted on the law enforcement vehicle. The drone can deploy on command, gather information about the suspect vehicle, interface with the vehicle's driver, and dock on the law enforcement vehicle once the traffic stop is complete. The officer does not have to risk his or her life to exit the law enforcement vehicle in order to collect documents, administer a breathalyzer test, or issue violations.

The drone of the present invention has a computer processor running software with integrated artificial intelligence, machine learning, and advanced computer vision. The drone is fitted with robotic arms, telepresence (speaker, microphone, camera), and sophisticated obstacle-avoidance sensors, including high resolution digital cameras, laser (LiDAR) systems and high-end computing systems that enable it to gain awareness of its surrounding by mapping and identifying objects in its path. The officer will receive appropriate training on how to use the drone, and considering the drone's sophisticated navigation systems, the training will be relatively simple.

The cost of the present invention is miniscule if compared to the alleviation of risk to a trained law enforcement officer's life. Every component for the present invention is already available on the market, and the computer software to implement this invention is not very complicated, as will be demonstrated in the description of the preferred embodiment.

DETAILED DESCRIPTION OF THE PREFERRED EMBODIMENT

The present invention relates to a drone for use during a law enforcement traffic stop. Rather than have the officer leave their vehicle, a drone can do everything that the law enforcement officer has to, without risking the officer's life. In the preferred embodiment, the drone is docked in a docking station on the law enforcement vehicle's roof, and can autonomously fly around the stopped suspect vehicle without any assistance from the officer. The officer does not have to control the drone's flight path, the officer only has to issue commands to the drone to perform required tasks.

The officer's vehicle's computer is connected remotely to the drone, and gets real-time updates. Once the officer initiates the drone, the drone autonomously chalks out the best flight path, and navigates to the suspect car, all the while avoiding traffic and other landscape obstacles.

Upon reaching the suspect vehicle, the drone hovers around the vehicle substantially at the same altitude where a law enforcement officer's head would be, scanning the interiors of the vehicle through the windows. The drone will make a circle around the suspect vehicle and check the vehicle's dashboard for any weapons, illicit, or dangerous products that may harm the law enforcement officer. This is carried out by the drone's visual HD cameras and onboard image processing hardware and software.

Once the drone has finished its fly-around, a two-way wireless communication channel can be established between the law enforcement officer and the suspect. The drone is equipped with a communication transmitter and receiver, camera, microphone and speaker.

The faces of the occupants are scanned by the drone and transmitted to the central server for processing. The server will match the faces of the occupants to a law enforcement database and retrieves a criminal history, if any.

The drone is fitted with a robotic arm that can interact with a driver. The arm is equipped with a breathalyzer and a document holding box. Depending on the reason for the traffic stop, the officer can use the drone's tools to check if the driver is driving under the influence, to collect the driver's license and registration from the suspect, and to issue and deliver a ticket to the driver.

Figure 1:
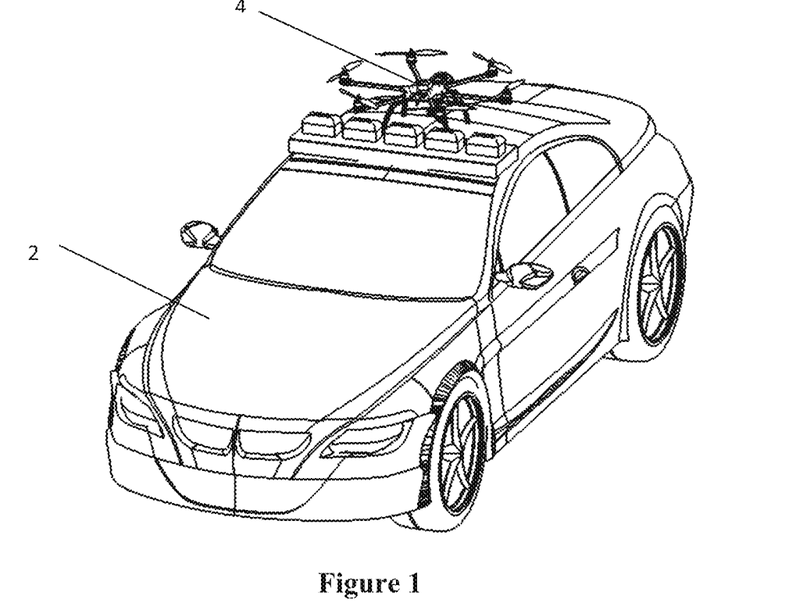
FIG. 1 shows the present invention mounted on a law enforcement vehicle.
Figure 2:
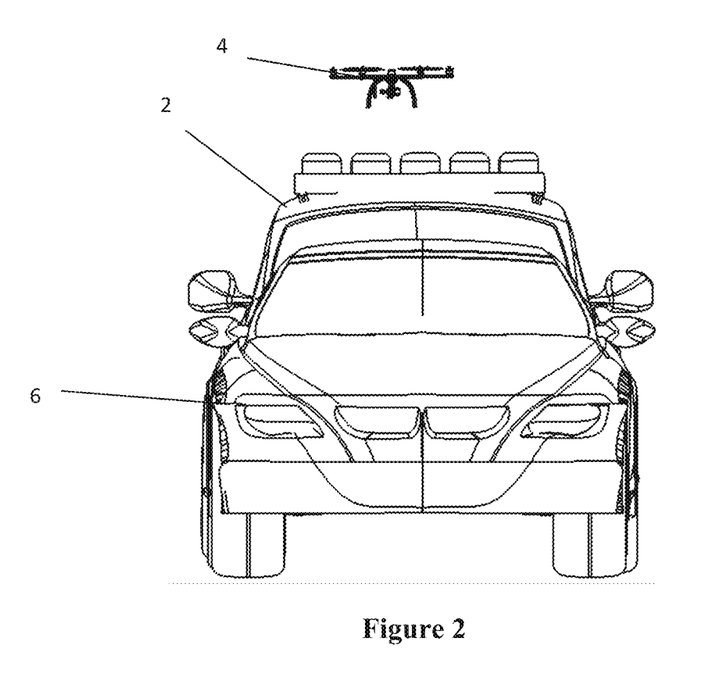
FIG. 2 shows a front view of the deployment of the present invention during the start of a traffic stop.

Referring now to drawings, FIG. 1 shows drone 4 docked in its station (not shown) on law enforcement vehicle 2. FIG. 2 shows the front view of a stopped suspect vehicle 6 with law enforcement vehicle 2 behind it, and drone 4 deployed by officer from its docking station.

Figure 3:
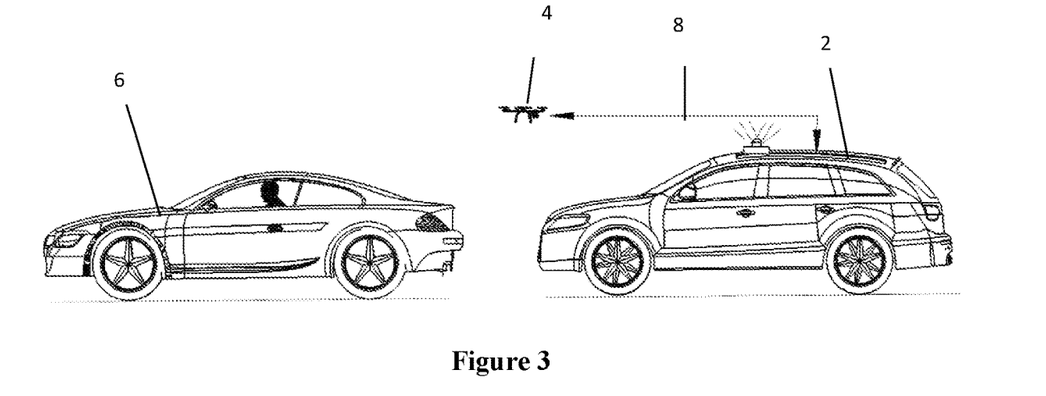
FIG. 3 shows a side view of FIG. 2.
Figure 4:
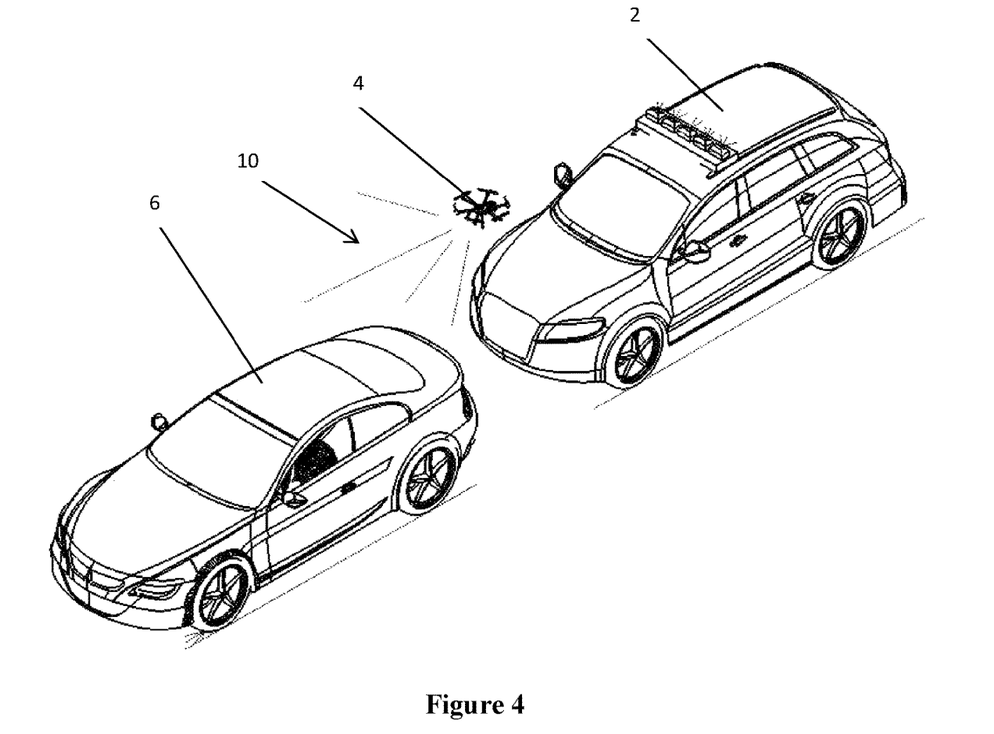
FIG. 4 shows the top perspective view of the preliminary flight path analysis stage of the drone of the present invention.

FIG. 3 is the side view of the 4 drone after it has been deployed by officer on a flight path 8 towards suspect vehicle 6 from law enforcement vehicle 2. FIG. 4 shows drone 4 implementing its spatial awareness and navigation systems 10, said systems 10 comprising cameras, LiDAR, GPS, sonar, or any other sensor that can assist the drone to map out its flight path 8 without encountering any obstacle. Navigation systems 10 are shown in more detail on FIG. 10.

Figure 5:
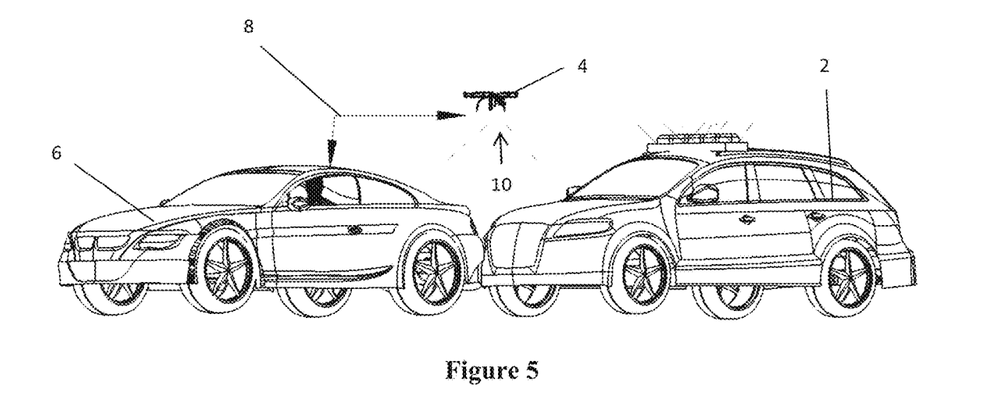
FIG. 5 shows a side perspective view of FIG. 4.
Figure 6:
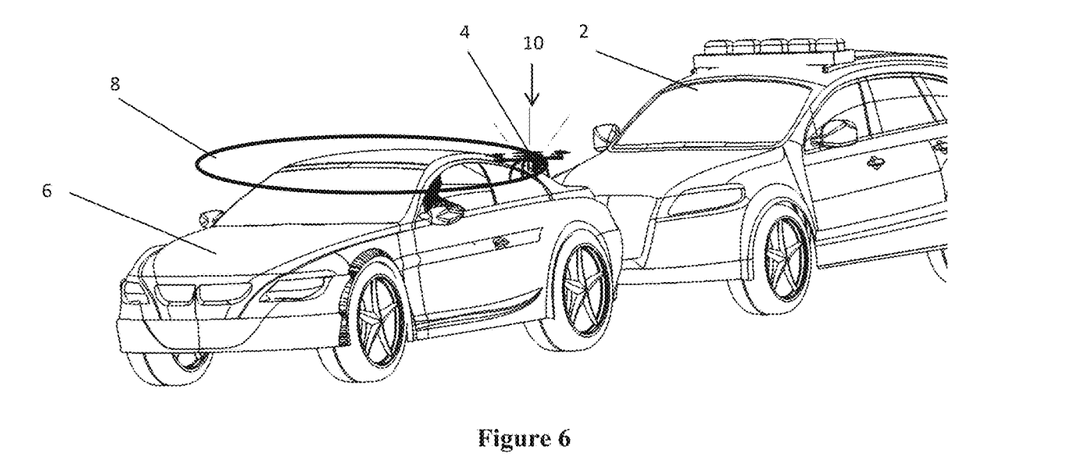
FIG. 6 shows a side perspective view of an inspection flight of a suspect vehicle.

FIG. 5 shows the drone 4 using systems 10 to establish a flight path 8 to the suspect vehicle 6's driver's side window. FIG. 6 demonstrates a flight path 8 by drone 4 to circle suspect vehicle 6 at substantially the same altitude where a law enforcement officer's head would be if the officer were to leave law enforcement vehicle 2. Drone 4 uses systems 10 to navigate flight path 8 to prevent hitting any obstacle while recording the visible view inside the vehicle with its telepresence array, shown in more detail on FIG. 10.

Figure 7:
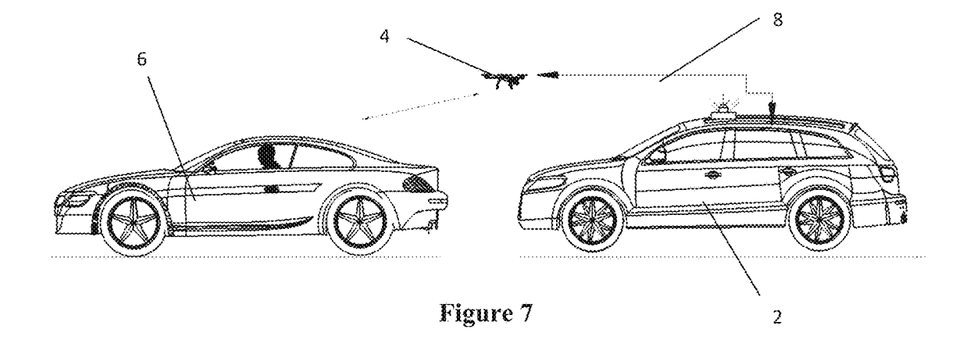
FIG. 7 shows a side view of the drone returning to its dock on the law enforcement vehicle.
Figure 8A:
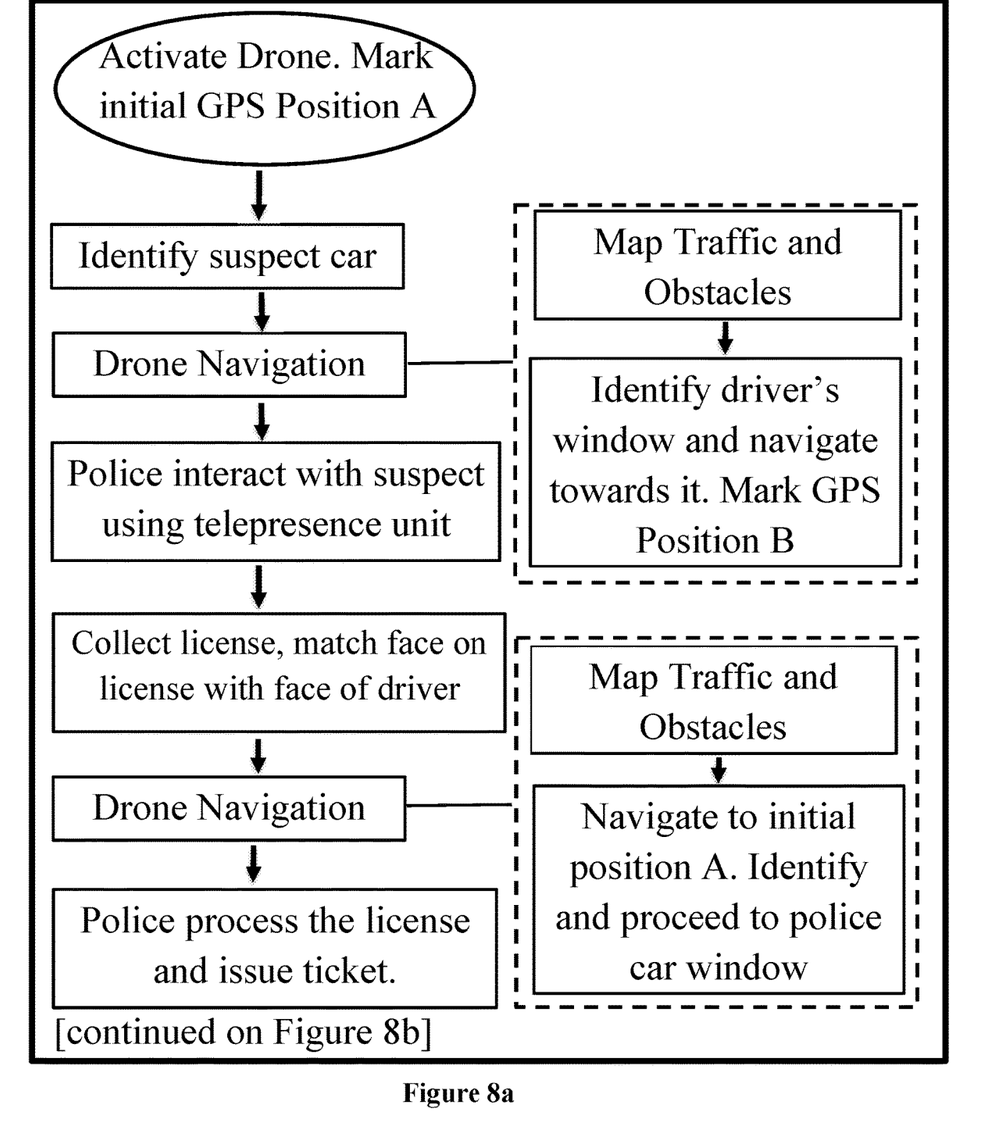
FIGS. 8a and 8b show a software flowchart of the drone's flight process.
Figure 8B:
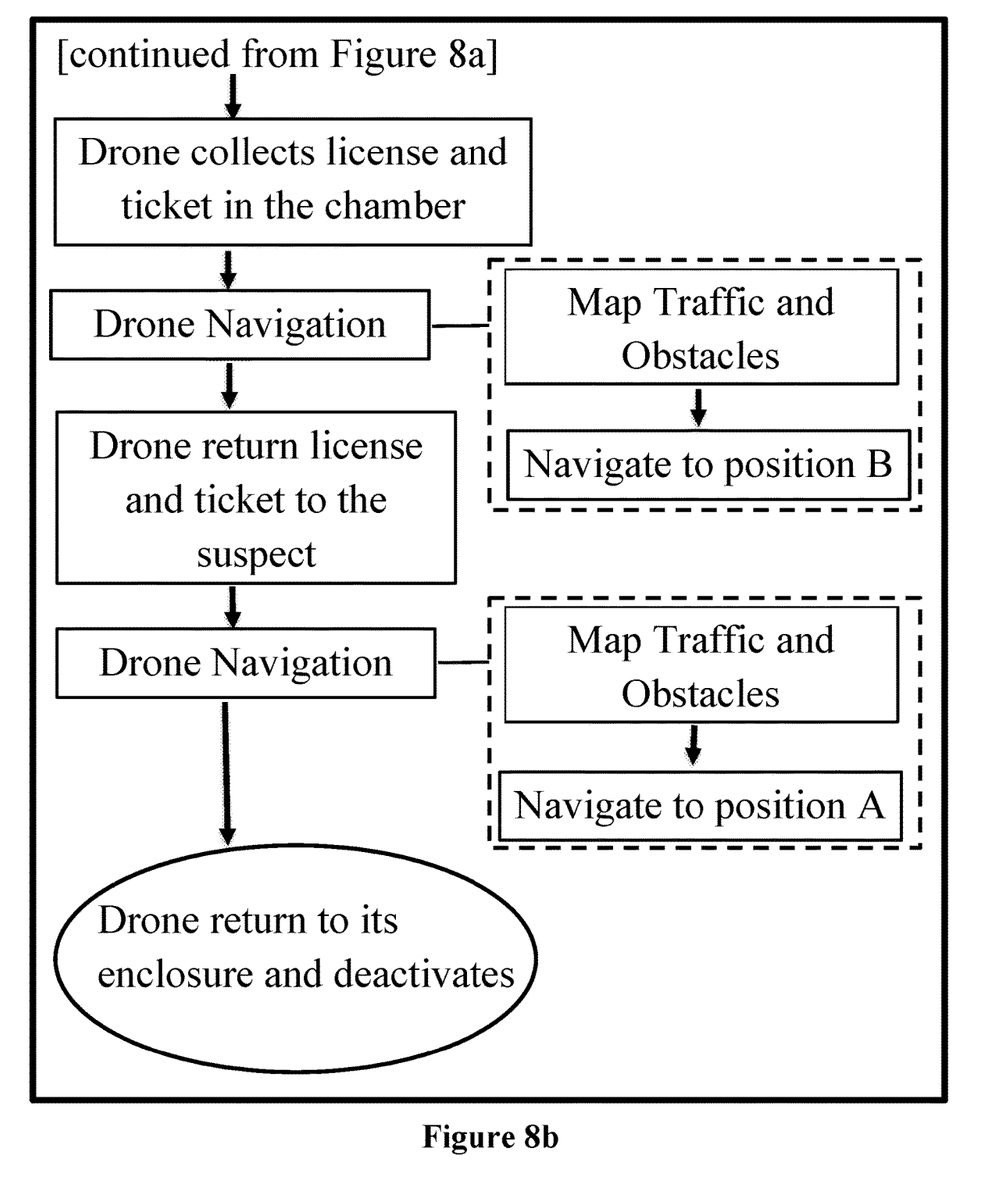

FIG. 7 shows drone 4 returning its docking station on law enforcement vehicle 2 via flight path 8. FIGS. 8a and 8b show is the flowchart of drone 4's software controller process.

Figure 9:
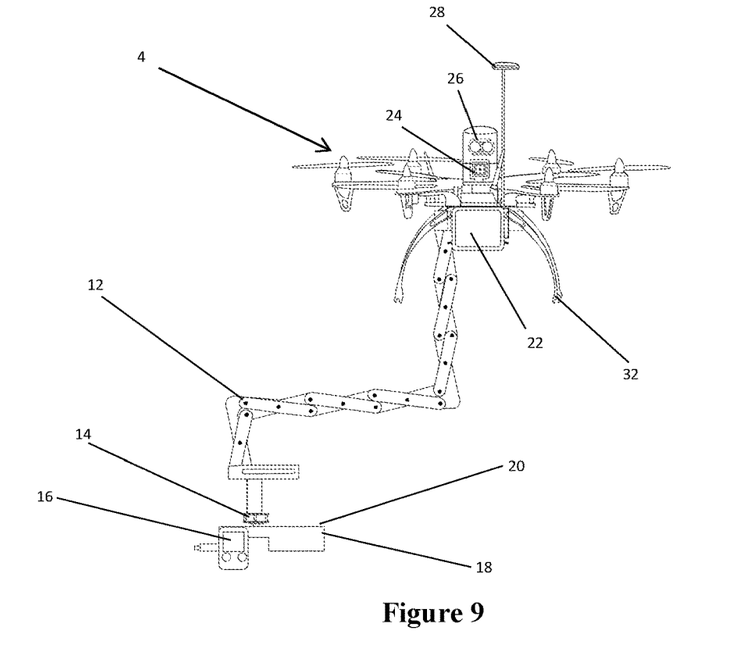
FIG. 9 shows the drone with an extended arm, telepresence system, breathalyzer, and secure chamber.

FIG. 9 shows drone 4, equipped with three distinct systems: navigation systems 10 comprising LiDAR 26, and GPS 28, telepresence systems comprising camera 24, microphone (not seen), speaker (not seen), and robotic arm 12 with a turning wrist 14 on its distal end that accommodates a breathalyzer 16, secure chamber 18 with a lid 20 for transporting documents to and from suspect vehicle 6 to law enforcement vehicle 2, and any other tools that may be used by a law enforcement officer.

Figure 10:
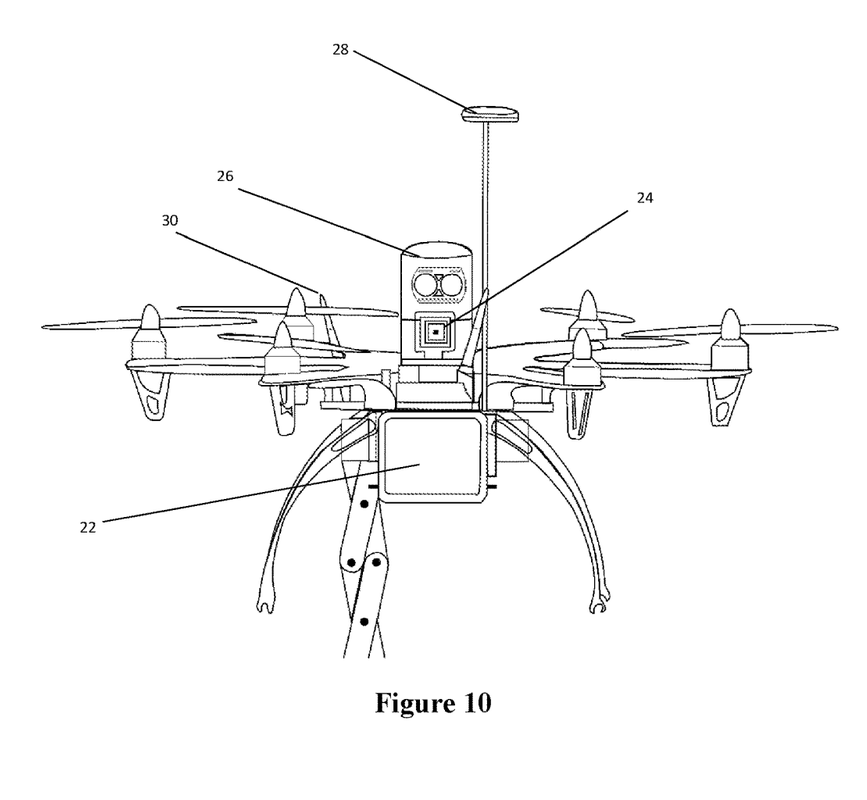
FIG. 10 shows a more detailed view of the telepresence and navigation systems.

FIG. 10 is a detailed view of the navigation system 10, namely a GPS antenna 28 and LiDAR 26, communication antennas 30, and telepresence system comprising camera 24 and screen 22. Not seen elements of the telepresence system are speaker and microphone.

Figure 11:
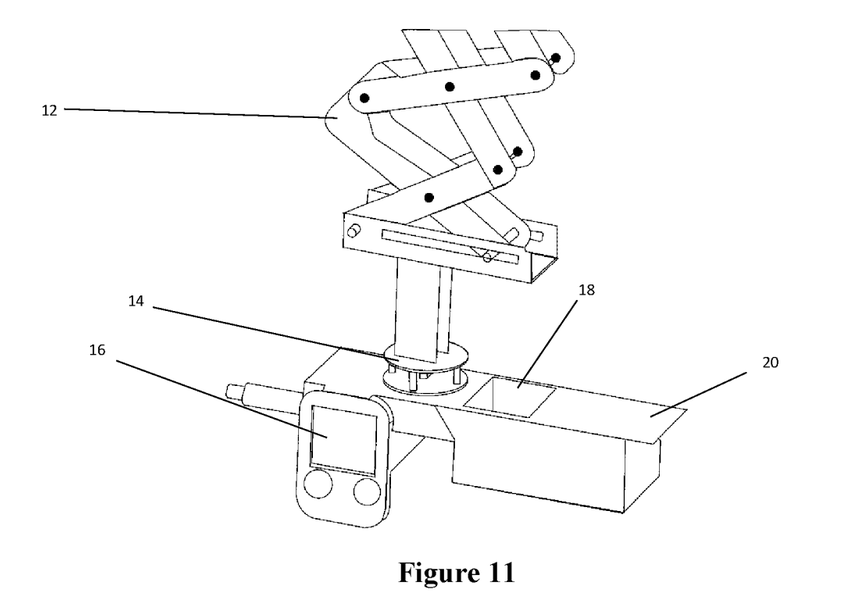
FIG. 11 shows a more detailed view of the tip of the arm with a breathalyzer and secure chamber.

FIG. 11 demonstrates the interfacing means that interact with a suspect vehicle 6's driver, namely a breathalyzer 16 and secure box 18 with lid 20, all mounted on arm 12's rotating wrist 14. Drone 4's landing/docking gear 32 is also seen on FIG. 11.

Figure 12:
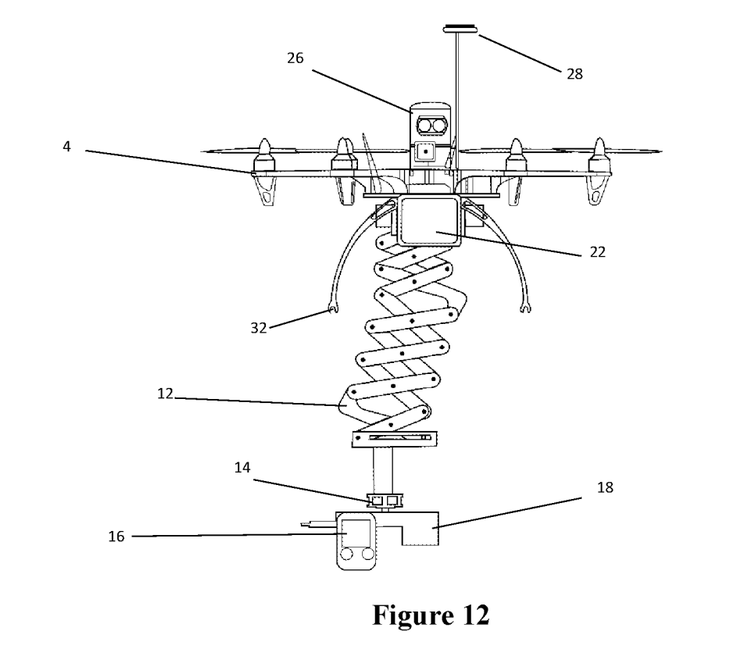
FIG. 12 shows drone with arm in the process of extending or retracting.

FIG. 12 shows drone 4 in hover mode with arm 12 retracting into stowage mode. Secure box 18 is closed, and transporting driver's documents to law enforcement car 2.

Figure 13:
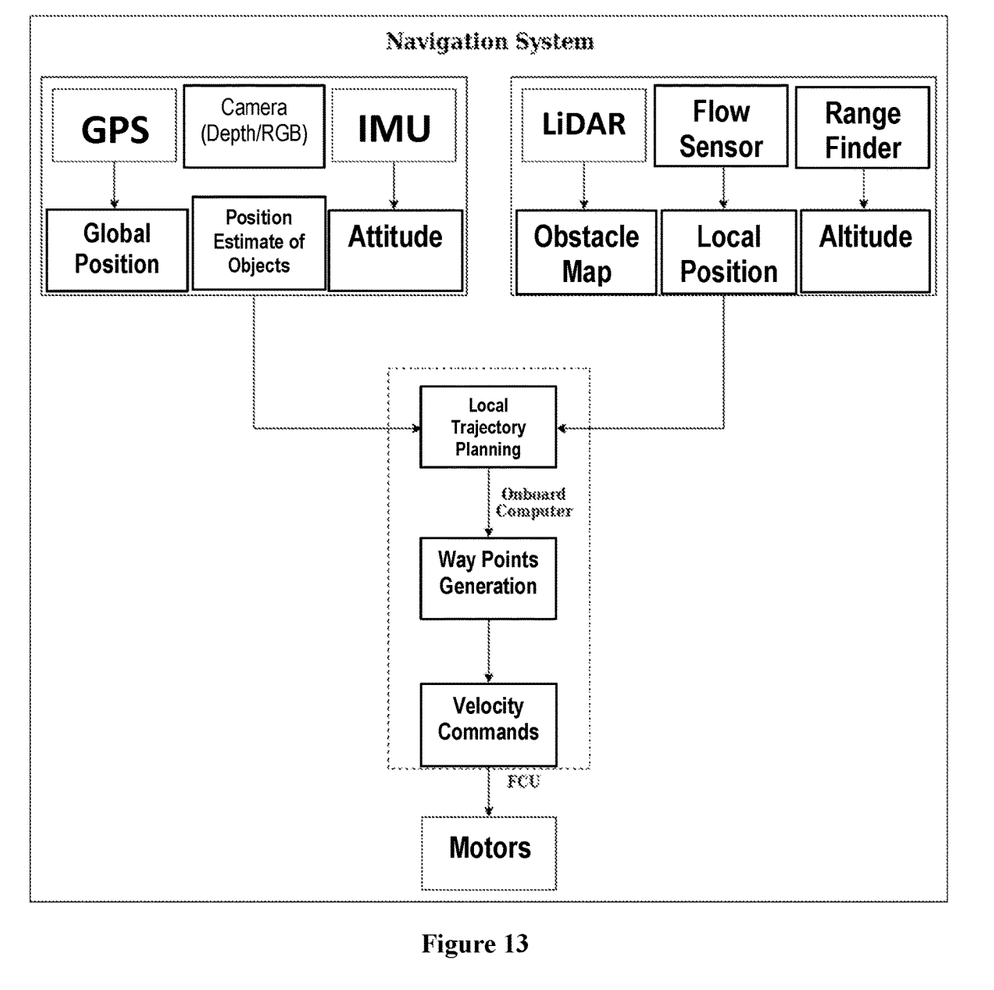
FIG. 13 shows a block diagram of the navigation system process.

FIG. 13 shows the navigation system 10's software and hardware block diagram, demonstrating the various elements that can be used for safe drone operation. System 10 can include sensors such as LiDAR, flow sensor, range finder, GPS, a camera, and an inertial measurement units sensor to measure pressure attitude. Working together, system 10 can provide input data for the onboard computer to plan a trajectory, generate waypoints, and adjust velocity of drone 4 during flight.

Figure 14:
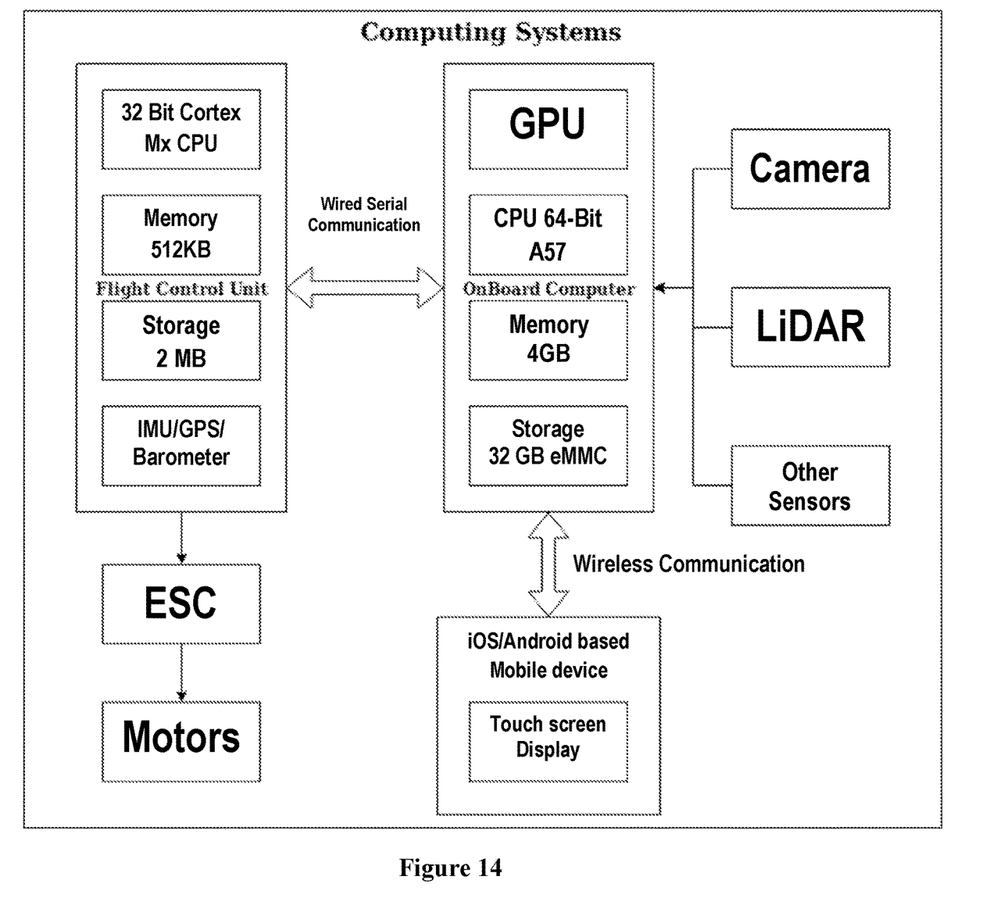
FIG. 14 shows a block diagram of the computing systems.
Figure 15:
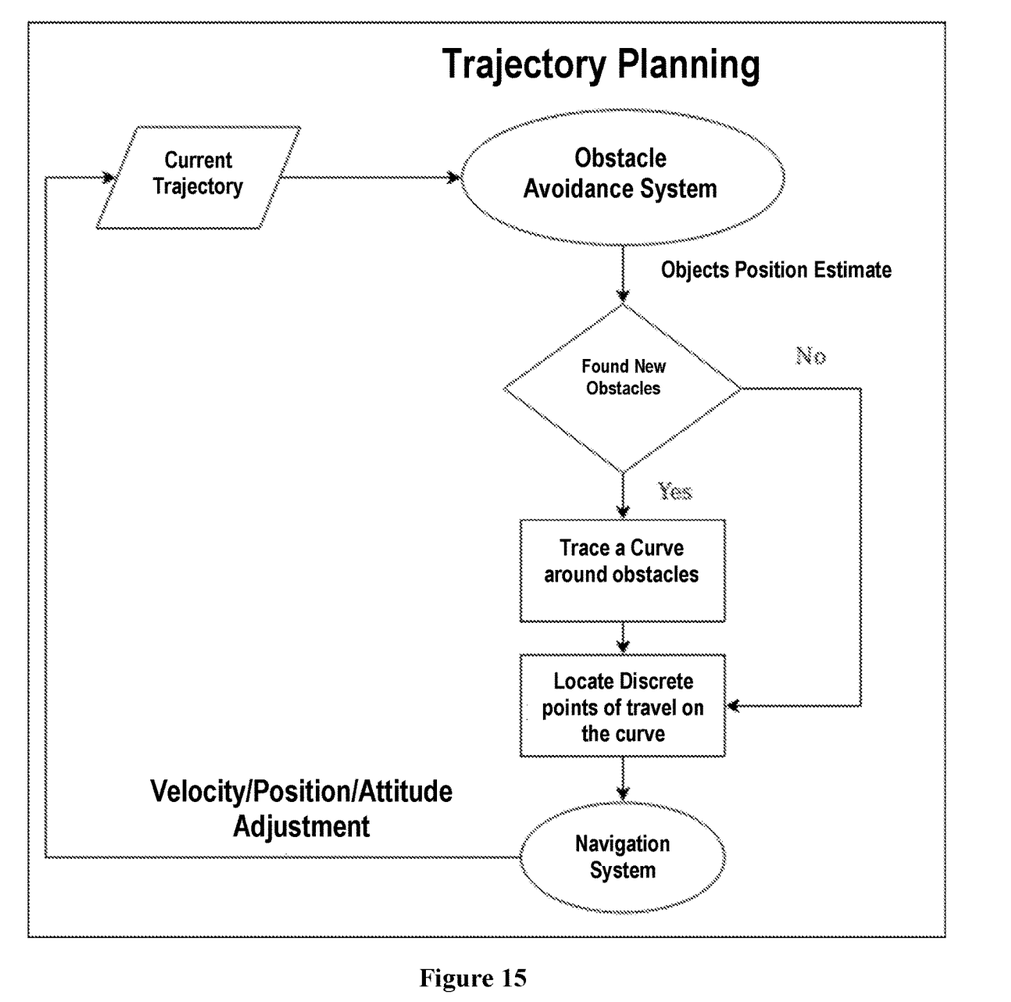
FIG. 15 shows a flowchart of trajectory planning.
Figure 16:
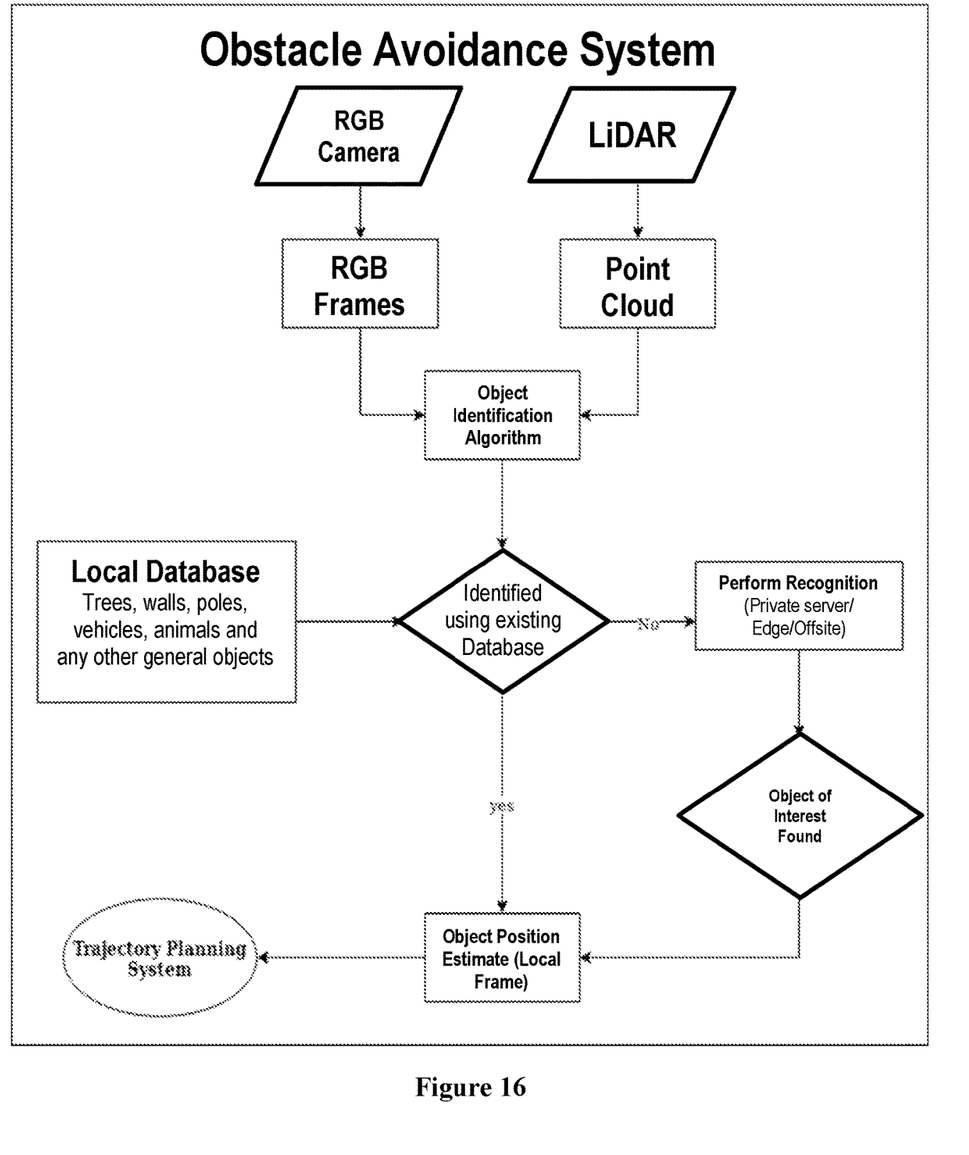
FIG. 16 shows a flowchart of the obstacle avoidance system.

FIG. 14 shows the block diagram for organization of drone 4's computing systems. FIG. 15 is one of the preferred embodiments for a flow-chart of drone 4's trajectory planning using navigation system 10 as an obstacle avoidance system. FIG. 16 shows a detailed block diagram of said obstacle avoidance system as facilitated by navigation system 10.

Figure 17:
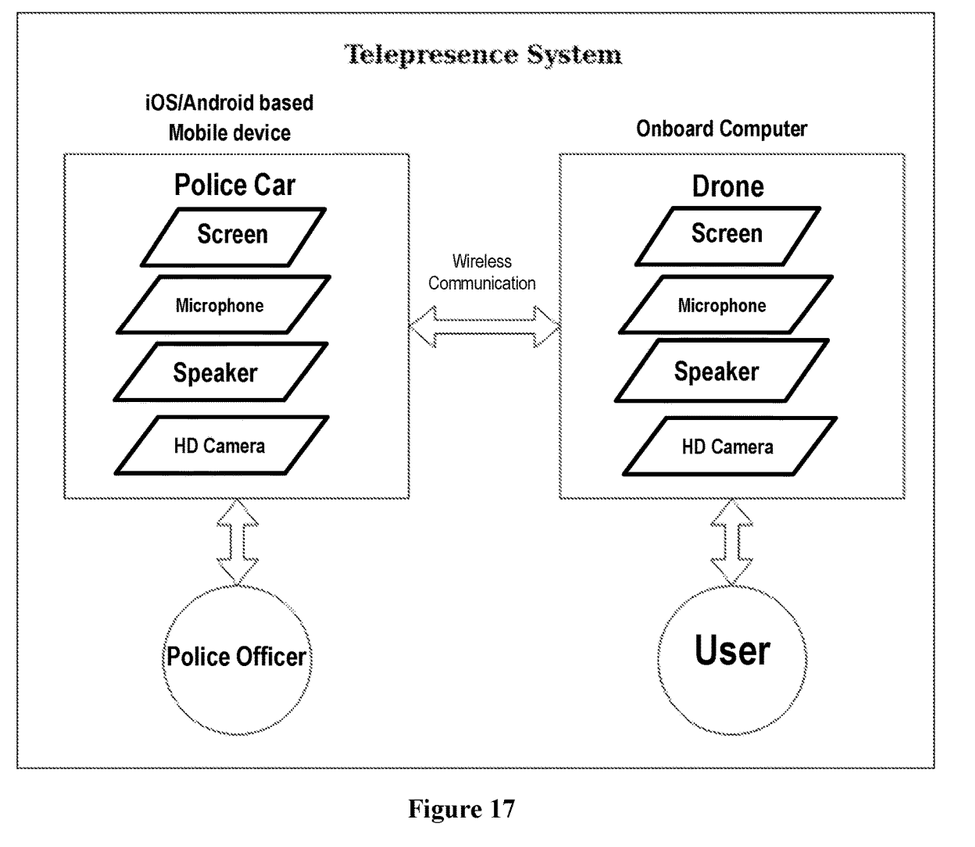
FIG. 17 shows a block diagram of the telepresence system.

FIG. 17 describes the telepresence system in a block-diagram. It shows a wireless communication protocol that allows the law enforcement officer to gather information and interact with suspect vehicle 6's driver while inside law enforcement car 2.

In practice, once the officer pulls over a suspect vehicle 6 and activates the drone 4, the drone starts its flight path 8 by marking its initial GPS position with system 10 so that it can return to the same place. Drone 4 takes off from its docking station on law enforcement vehicle 2 and starts collecting data using systems 10, namely the LiDAR 26 and camera 24, of its surrounding environment. Drone 4 embeds both the depth data from LiDAR 26 and RGB data from camera 24, and creates a 3-dimensional view of its surrounding, called "RGBD data". It also keeps track of its position using GPS 28 and various inertial sensors from systems 10. All this data is transmitted to the computing devices of law enforcement officer's vehicle 2.

Next, drone 4 runs an object recognition algorithm for any vehicles on the road and targets the suspect vehicle 6 that is straight ahead. The law enforcement officer has an option to change the target if required. Then, drone 4 scans for all the obstacles in front of it. It plans a flight path 8 to reach the target 6. It starts on its path 8 and keeps updating the data from its sensors 10. The new RGBD data is registered with previous data and map is created.

The obstacle detection algorithm is run frequently to identify dynamic obstacles that can intrude in drone 4's path. Flight path 8 is updated accordingly to avoid these obstacles. Once drone 4 reaches the top of the target car 6, it hovers around car 6 to generate a 3D map of the car with systems 10. From this, it identifies the position of the driver's window and navigates to it.

The law enforcement officer can now interact with driver using the telepresence unit (seen on FIG. 10), namely speaker and video display 22. Drone 4 scans the face of the driver and tries to match the face of the driver with the driver's license. It also transmits the scan to a central server to run facial analytics and discern if the suspect has any criminal history.

Via the telepresence system, the driver is instructed by the officer to present the driver's license to the telepresence camera 24 of drone 4. Drone 4 will determine if the face of the driver matches the face on the license.

The robotic arm 12, shown in more detail on FIG. 9, is activated from its collapsed position by unfolding. Rotating wrist 14 located at arm 12's distal end turns and presents open secure chamber 18 to the driver of suspect vehicle 6 to collect the driver's license and any other relevant documents from the driver. Lid 20 of secure chamber 18 is electronically controlled by the processor. The algorithm ensures that no part of the driver's body is in proximity of chamber 18 before closing lid 20 to prevent pinching fingers or any other injury to the driver. Robotic arm 12 then collapses back into its folded position.

Drone 4 then repeats the process of obstacle detection, path 8 planning and navigation to reach law enforcement car 2, whose position has been saved previously. Drone 4 hovers around law enforcement car, generates a 3D model, identifies the officer's window and navigates to it. Robotic arm 12 unfolds, chamber 18 opens, and the license is retrieved by the officer who is safely inside the law enforcement vehicle 2.

Once the officer processes the license and issues any ticket for traffic violations, he places them both in drone 4's secure chamber 18. Arm 12 returns to its folded position and chamber lid 20 is secured. Subsequently, drone 4 navigates to suspect vehicle 6 as before, presents an open secure chamber 18 to the driver so that the driver can retrieve the ticket, documents and driver's license, and drone 4 finally returns to its enclosure on top of law enforcement vehicle 2.

It should be noted that drone 4 will not be equipped with sensors that may violate any Unlawful Search and Seizure laws, depending on the jurisdiction. Drone 4 is the proxy representation of the law enforcement officer, equipped with only the tools that are available to a law enforcement officer.

The invention claimed is:

1. A drone adapted to be securely docked in a dockage station on a law enforcement vehicle, said drone comprises:
    obstacle-avoidance sensors,
    a processor running artificial intelligence and machine learning software,
    navigation system,
    telepresence system,
    a wireless receiver and transmitter,
    a breathalyzer and a secure chamber with a lid for transporting documents, said drone is adapted to fly autonomously around a stopped suspect vehicle,
    wherein the drone is adapted to be operated by a law enforcement officer who issued commands to said drone to perform required tasks,
    wherein said artificial intelligence and machine learning software is provided to assist said officer in making contact with an occupant of said stopped suspect vehicle,
    wherein said drone implements spatial awareness and navigation systems to avoid obstacles and interface with said occupant of said stopped suspect vehicle and said law enforcement officer without causing injury to people or property, and
    wherein said breathalyzer and said secure chamber with a lid for transporting documents between said officer and said suspect vehicle's occupant assist said officer to administer a sobriety test, gather said occupant's documents, and deliver a traffic violation ticket to said occupant.

2. A drone according to claim 1, wherein said breathalyzer and secure chamber with a lid for transporting documents are located on a distal end of a robotic arm, said robotic arm being attached to said drone.

3. A drone according to claim 1, wherein said obstacle-avoidance sensors comprise a camera and a laser system, said sensors providing data to said processor to enable said drone to be aware of its surroundings, as well as mapping and identifying objects in its path.

4. A drone according to claim 1, wherein said drone is remotely connected to a computer in said law enforcement vehicle to get real-time updates.

5. A drone according to claim 1, wherein said telepresence system includes a speaker, a microphone, a screen and a camera.

6. A drone according to claim 1, wherein said drone is adapted to allow said officer to initiate said drone to automatically plan the best flight path and to navigate to said suspect car, wherein said drone flies around suspected vehicle, and said drone establishes a two-way wireless communication channel between said law enforcement vehicle and said suspect vehicle.

7. A drone according to claim 5, wherein a face of said suspect occupant is adapted to be scanned by said camera of said drone and transmitted to a remote location for processing and verification by a central law enforcement database.

8. A drone according to claim 1, wherein said navigation system comprises cameras, a Light Detection and Ranging system commonly known as LiDAR, GPS, and sonar sensors, that assist said drone to map out its flight path without encountering obstacles, and wherein said drone uses said system to navigate said flight path to prevent hitting obstacles while recording a visible view inside said vehicle with said telepresence system.

9. An unmanned aerial system adapted to be securely docked on a law enforcement vehicle, said unmanned aerial system comprises:
    obstacle-avoidance sensors comprising a camera, sonar and Light Imaging Detection and Ranging (LIDAR) system,
    a processor running artificial intelligence and machine learning software, navigation system comprising GPS receiver, and Light Imaging Detection and Ranging (LIDAR) system, telepresence system comprising a microphone, speaker, screen and camera, a wireless receiver and transmitter, and a robotic arm with a breathalyzer and a secure chamber with a lid for transporting documents located at a distal end of said robotic arm, said unmanned aerial system is adapted to fly autonomously around a stopped suspect vehicle, wherein the drone is adapted to be operated by a law enforcement officer who issued commands to said drone to perform required tasks, wherein said artificial intelligence and machine learning software is provided to assist said officer in making contact with an occupant of said stopped suspect vehicle, wherein said unmanned aerial system implements spatial awareness and navigation systems to avoid obstacles and interface with said occupant of said stopped suspect vehicle and said law enforcement officer without causing injury to people or property.

\* \* \* \* \*